(12) United States Patent
Meridew et al.

(10) Patent No.: US 7,572,294 B2
(45) Date of Patent: Aug. 11, 2009

(54) METHOD AND APPARATUS FOR REMOVING AN ACETABULAR BEARING

(75) Inventors: Jason D Meridew, Syracuse, IN (US); Troy W Hershberger, Winona Lake, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 10 days.

(21) Appl. No.: 11/714,991

(22) Filed: Mar. 7, 2007

(65) Prior Publication Data
US 2008/0221699 A1  Sep. 11, 2008

(51) Int. Cl.
*A61F 2/32* (2006.01)
(52) U.S. Cl. .................................. 623/22.12; 623/22.2
(58) Field of Classification Search ............ 623/22.11, 623/22.12, 22.15, 22.17–22.21, 22.28, 22.29; 606/90–92, 99
See application file for complete search history.

(56) References Cited

U.S. PATENT DOCUMENTS

| | | | |
|---|---|---|---|
| 4,908,033 A | 3/1990 | Frey et al. | |
| 5,049,158 A | 9/1991 | Engelhardt et al. | |
| 5,092,897 A | 3/1992 | Forte | |
| 5,222,984 A | 6/1993 | Forte | |
| 5,226,917 A | 7/1993 | Schryver | |
| 5,310,408 A | 5/1994 | Schryver et al. | |
| 5,314,487 A | 5/1994 | Schryver et al. | |
| 5,314,491 A | 5/1994 | Thongpreda et al. | |
| 5,425,778 A * | 6/1995 | Zichner et al. ............ | 623/22.29 |
| 5,658,348 A | 8/1997 | Rohr, Jr. | |
| 5,725,587 A | 3/1998 | Garber | |
| 5,725,591 A | 3/1998 | DeCarlo, Jr. et al. | |
| 5,885,301 A | 3/1999 | Young et al. | |
| 5,928,287 A | 7/1999 | Keller et al. | |

(Continued)

FOREIGN PATENT DOCUMENTS

DE  19654409 C1 *  4/1998

(Continued)

OTHER PUBLICATIONS

Smith&nephew, Orthopaedic Catalog, Prepared for: Hip Systems—Acetabular Options, Smith & Nephew, Inc., Oct. 16, 2003 (24 pages).

(Continued)

*Primary Examiner*—Thomas J Sweet
*Assistant Examiner*—Yashita Sharma
(74) *Attorney, Agent, or Firm*—Harness, Dickey (57) ABSTRACT

A system for replacing a portion of a hip joint can include a cup having an outer surface and an inner surface. A bearing can include an outer bearing surface and an inner articulating surface. The outer bearing surface can be positioned adjacent to the cup. A ring can be selectively disposed between the cup and the bearing. The ring can define an annular body having a slit formed therein. A removal tool can define a proximal end and a distal end. The distal end can define a ring engaging surface and a bearing engaging surface. The ring engaging surface can be adapted to engage the ring at the slit such that the ring expands radially from a locked position away from engagement with the bearing to an unlocked position. The bearing engaging surface can be adapted to engage the bearing and urge the bearing away from the cup.

21 Claims, 9 Drawing Sheets

U.S. PATENT DOCUMENTS

| | | | |
|---|---|---|---|
| 5,935,175 | A | 8/1999 | Ostiguy, Jr. et al. |
| 5,938,701 | A | 8/1999 | Hiernard et al. |
| 6,013,082 | A | 1/2000 | Hiernard et al. |
| 6,063,123 | A | 5/2000 | Burrows et al. |
| 6,132,469 | A | 10/2000 | Schroeder |
| 6,916,342 | B2 | 7/2005 | Frederick et al. |
| 6,986,792 | B2 | 1/2006 | McLean et al. |
| 2002/0147499 | A1 | 10/2002 | Shea et al. |
| 2003/0187512 | A1 | 10/2003 | Frederick et al. |
| 2004/0054418 | A1 | 3/2004 | McLean et al. |
| 2004/0177662 | A1* | 9/2004 | Bosse ............... 70/465 |
| 2004/0204767 | A1 | 10/2004 | Park et al. |
| 2004/0225369 | A1 | 11/2004 | Lakin et al. |
| 2005/0246031 | A1 | 11/2005 | Frederick et al. |
| 2006/0217814 | A1 | 9/2006 | Lambert et al. |
| 2007/0016218 | A1* | 1/2007 | Winslow et al. ............... 606/99 |
| 2007/0239283 | A1 | 10/2007 | Berger et al. |

FOREIGN PATENT DOCUMENTS

| | | |
|---|---|---|
| EP | 0611008 | 8/1994 |

OTHER PUBLICATIONS

Smith&nephew, Reflection Interfit, web page at http://www.smithnephew.com/us/node.asp?NodeId+2914, printed Aug. 16, 2006 (2 pages).

International Search Report and Written Opinion mailed Jul. 23, 2008 for PCT/US2008/003045.

* cited by examiner

METHOD AND APPARATUS FOR REMOVING AN ACETABULAR BEARING

FIELD

The present disclosure relates to implants and more particularly to a method and apparatus for removing an acetabular bearing.

INTRODUCTION

A natural hip joint may undergo degenerative changes due to a variety of etiologies. When these degenerative changes become so far advanced and irreversible, it may ultimately become necessary to replace all or portions of a natural hip with a prosthetic hip. In one example, a modular acetabular prosthesis may be implanted in an acetabulum of a patient. With a modular prosthesis, an orthopedic surgeon can implant an appropriate acetabular cup and select an appropriate bearing to attach to the acetabular cup. Modular bearings are often readily removable and, in such cases, they have the further advantage of facilitating revision surgery, which may become necessary in cases of traumatic injury or bearing surface wear, by enabling replacement of the bearing without removing the acetabular cup. A need exists for a system to facilitate efficient removal of the bearing from the acetabular cup.

SUMMARY

A system for replacing a portion of a hip joint can include a cup having an outer surface and an inner surface. The outer surface can be adapted to engage an acetabulum. A bearing can include an outer bearing surface and an inner articulating surface. The outer bearing surface can be positioned adjacent to the cup. A ring can be selectively disposed between the cup and the bearing. The ring can define an annular body having a slit formed therein. The ring can be movable between a locked position wherein the ring retains the bearing relative to the cup and an unlocked position. A removal tool can define a proximal end and a distal end. The distal end can define a ring engaging surface and a bearing engaging surface. The ring engaging surface can be adapted to engage the ring at the slit such that the ring expands radially from the locked position away from engagement with the bearing to the unlocked position. The bearing engaging surface can be adapted to engage the bearing and urge the bearing away from the cup.

According to additional features the cup can define an upper rim portion having a first slot formed radially thereon. The slot can further define a ramped surface sloping downward from an outboard portion to an inboard portion. The ring can define a pair of fingers formed at opposing portions of the slit. The fingers can be adapted to locate at the first slot in the cup in the locked position. The upper rim of the cup can further define a second slot formed therein and adapted to locate an annular protrusion defined on the ring in the locked position.

According to other features, the ring engaging surface of the removal tool defines a pair of sloped surfaces adapted to slidably engage the pair of fingers and thereby spread the ring radially toward the unlocked position. The distal end of the tool can be accommodated by the ramped surface of the slot such that the bearing engaging surface engages the bearing. An upper portion of the bearing and the rim of the cup can define complementary interlocking portions adapted to inhibit rotation of the bearing within the cup in the locked position.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the embodiment(s) is merely exemplary in nature and is in no way intended to limit the invention, its application, or uses.

Figure 1:
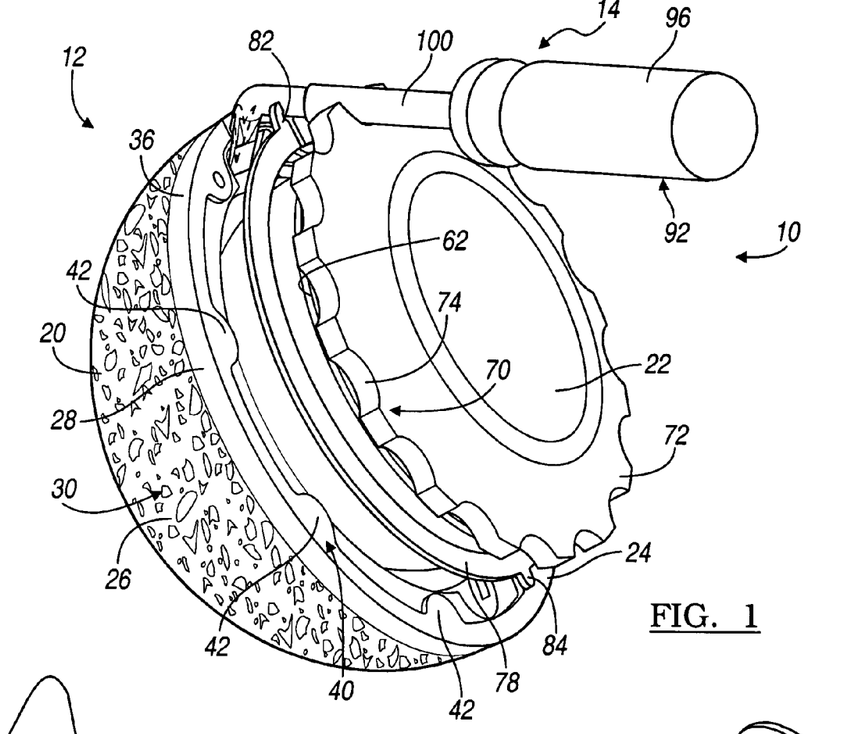
FIG. 1 is a perspective view of a system according to the present teachings including an acetabular cup assembly and a removal tool, the acetabular cup assembly including a cup, a bearing and a ring.

With initial reference to FIG. 1, a system for replacing a portion of a hip joint is shown and generally identified at reference 10. The system 10 can generally include an acetabular cup assembly 12 and a removal tool 14. The acetabular cup assembly 12 can include an acetabular cup 20, a liner or bearing 22 and a ring 24. As will become appreciated, the ring 24 can be adapted to retain the bearing 22 relative to the acetabular cup 20 in a locked position. The removal tool 14 can be adapted to engage the ring 24 and operatively spread the ring 24 to an unlocked position, and subsequently lever the bearing 22 away from the acetabular cup 20.

Figure 4:
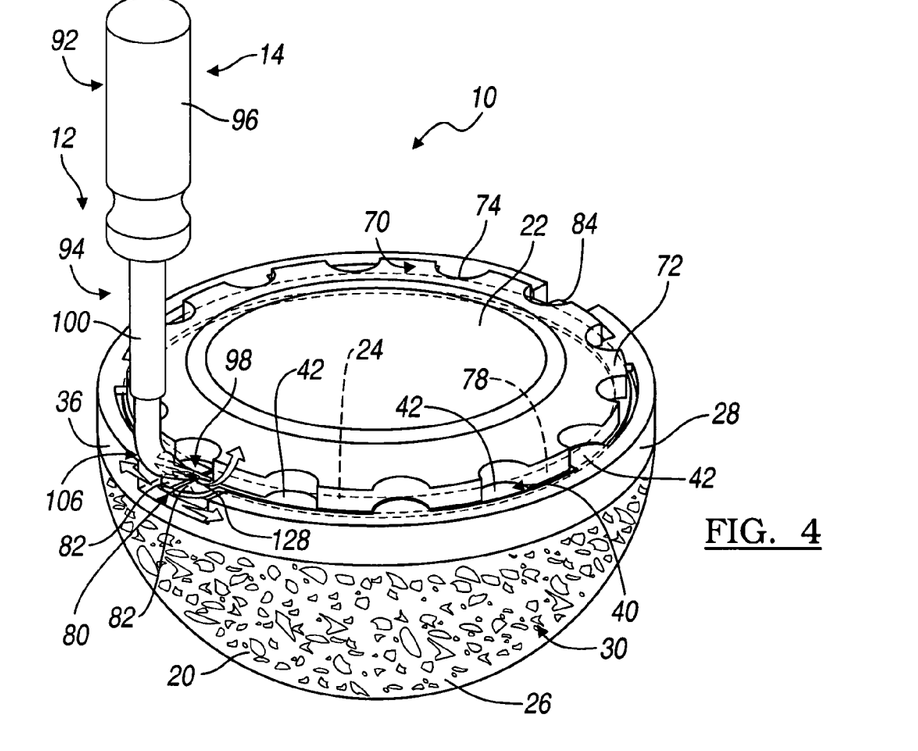
FIG. 4 is a perspective view of the acetabular cup assembly shown with the bearing in a locked position within the acetabular cup and the distal end of the removal tool initially engaged with a slit defined in the ring.
Figure 5:
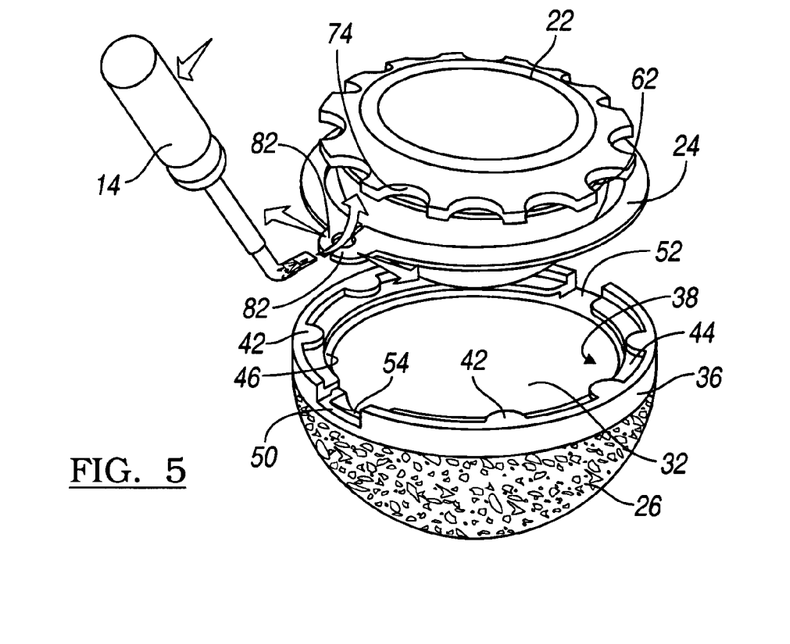
FIG. 5 is a perspective view of the acetabular cup assembly and removal tool subsequent to removal of the ring and bearing.

With particular reference now to FIGS. 1, 4 and 5, the acetabular cup assembly 12 will be further described. In general, the acetabular cup 20 may include a porous metal portion 26 and a solid metal portion 28. The porous metal portion 26 generally may be formed on an outer bone engaging surface 30 of the acetabular cup 20, while the solid metal portion 28 may be formed on an inner surface 32 (FIG. 5). The porous metal and solid metal portions 26 and 28, respectively, may comprise biocompatible metal, such as stainless steel, titanium, titanium alloys, and cobalt-chromium alloys. In one example, the porous metal portion 26 may be formed of porous metal defining about 60-70% porosity. In one example, the porous metal portion 26 can be sintered onto the solid metal portion 28. The solid metal portion 28 may define a solid rim 36 and a bearing engaging surface 38. In one example, the solid rim 36 may be defined entirely through a thickness of the acetabular cup 20 at the solid rim 36. While not specifically shown, an interface between the porous metal portion 26 and the solid metal portion 28 may comprise interlocking annular rings and pockets. A discussion of a similar acetabular cup may be found in co-pending U.S. patent application Ser. No. 11/111,123, which is hereby incorporated by reference.

Figure 6:
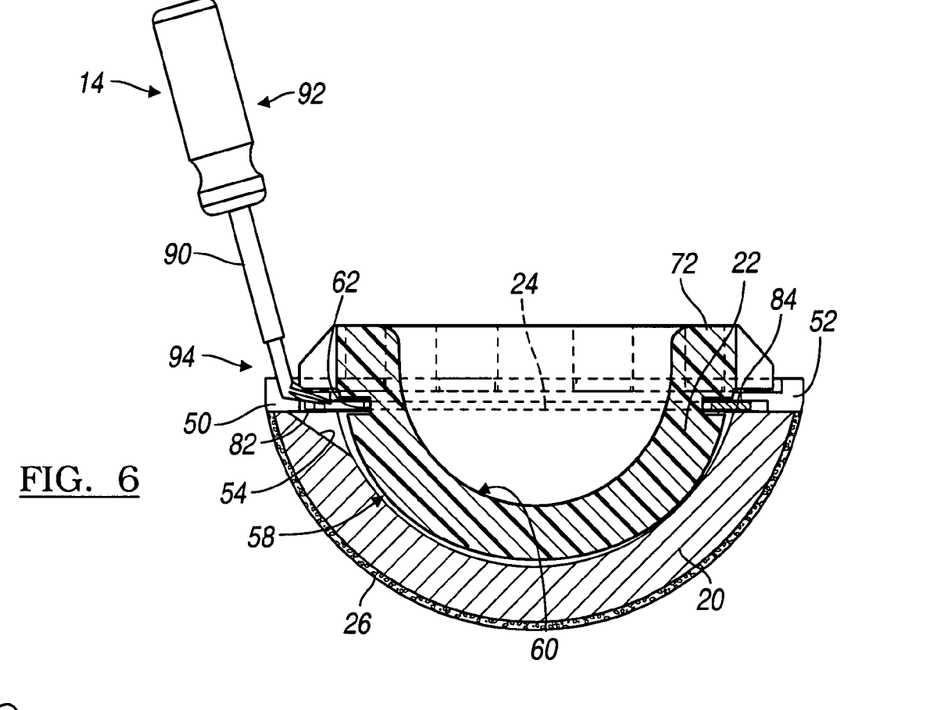
FIG. 6 is a sectional view taken along line 6-6 of FIG. 3 shown with the distal end of the tool initially engaging the ring.

The solid rim 36 can define a first interlocking portion 40. In the example shown, the first interlocking portion 40 is in the form of lobbed fingers 42 defined around an upper perimeter of the solid rim 36. The lobbed fingers 42 can be generally raised relative to an annular shoulder 44 (FIG. 5) defined around the solid rim 36. The solid metal portion 28 can further define an inboard annular groove 46 formed around the bearing engaging surface 38. The solid rim 36 can further include a first and second slot 50 and 52, respectively. In one example, the first and second slots 50 and 52 may be formed at diametrically opposing locations on the solid rim 36. The first slot 50 can include a sloped or ramped surface 54 (as best shown in FIG. 6). The ramped surface 54 can slope downward generally from an outboard portion to an inboard portion of the acetabular cup 20. The second slot 52 can define a surface generally parallel to the annular shoulder 44.

Figure 9:
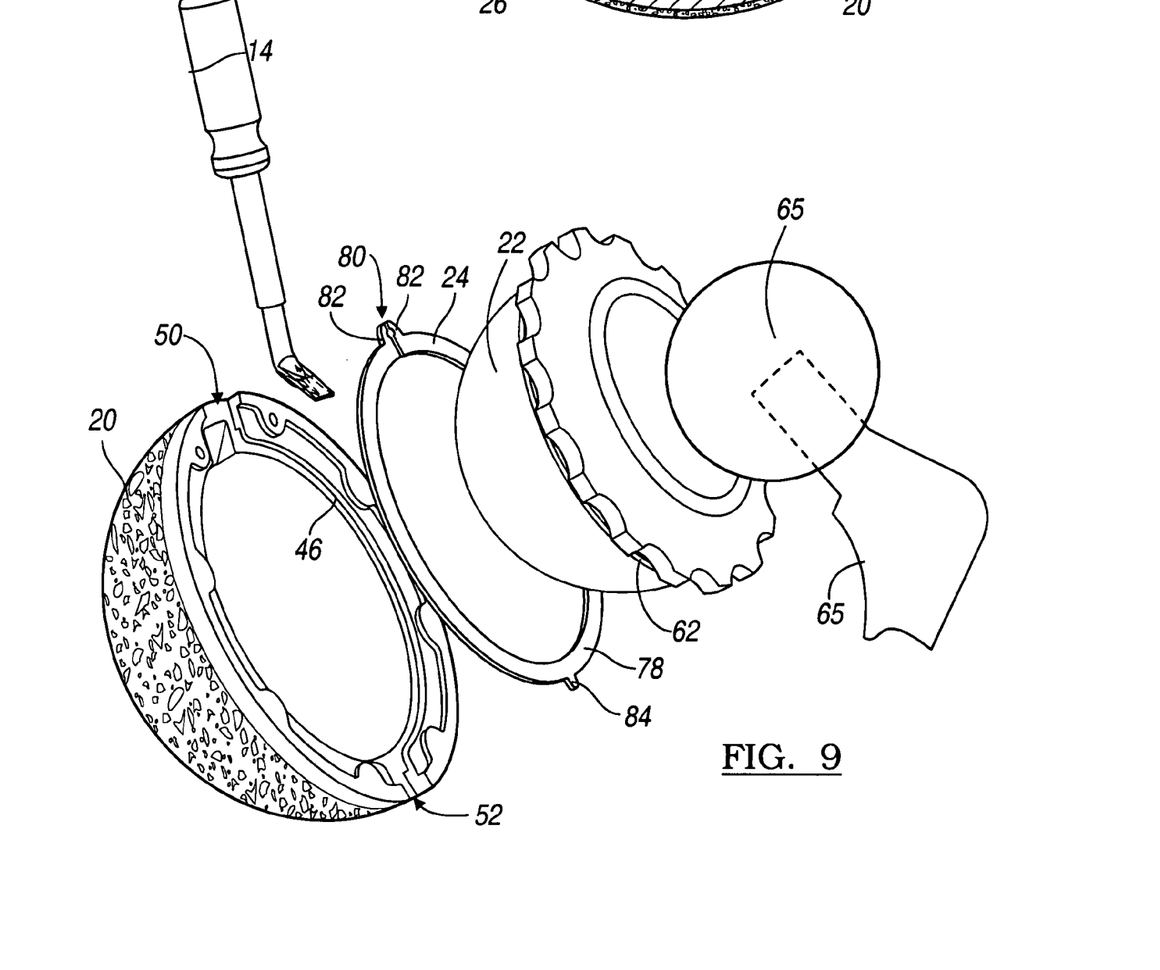
FIG. 9 is an exploded side perspective view of the system of FIG. 1.
Figure 10:
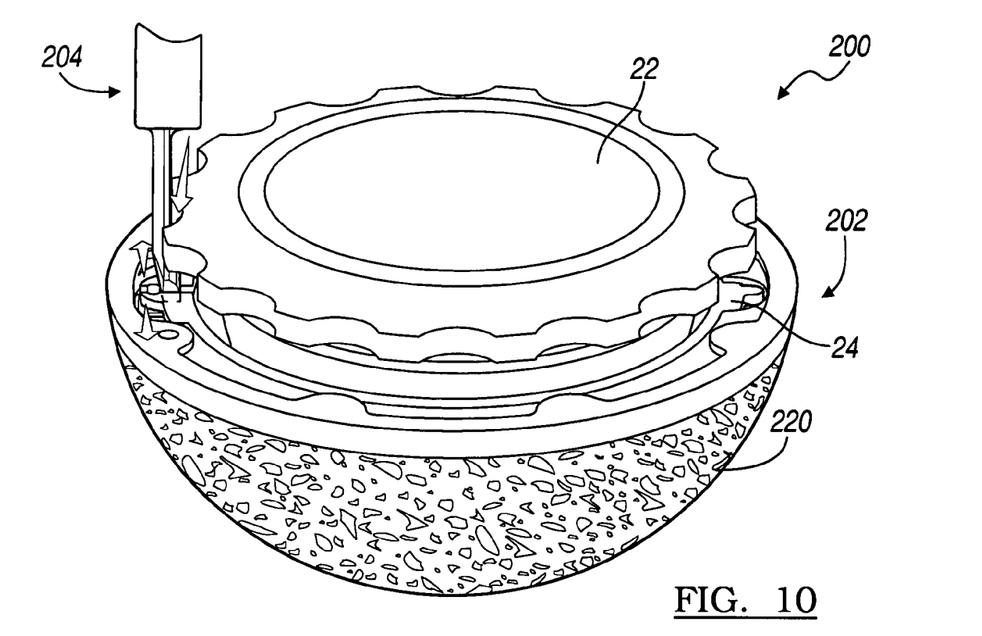
FIG. 10 is a perspective view of a system according to additional features of the present teachings including an acetabular cup assembly and a removal tool, the acetabular cup including a cup, a bearing and a ring.
Figure 11:
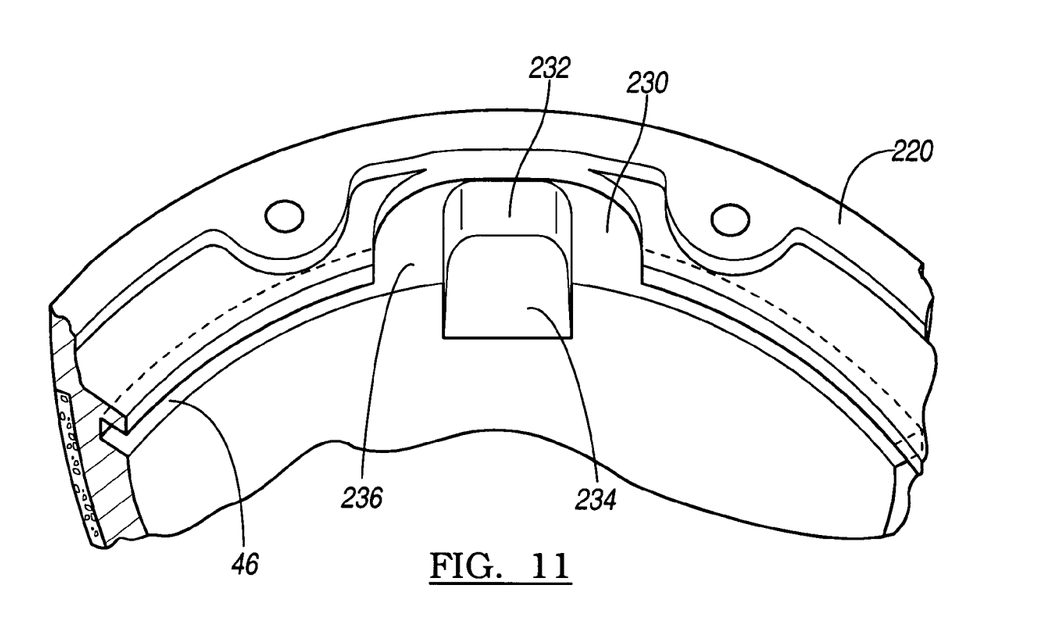
FIG. 11 is a perspective view of a notch formed in the acetabular cup of FIG. 10.

The bearing 22 will now be described in greater detail. The bearing 22 may be formed of polyethylene or other suitable bearing material. The bearing 22 can generally include an outer cup engaging surface 58 and an inner femoral component engaging surface 60. An outboard annular groove 62 can be formed around the outer cup engaging surface 58. The outer cup engaging surface 58 can be generally convex, while the inner femoral component engaging surface 60 can be generally concave. The bearing 22 can define a uniform thickness, below the outboard annular groove 62 (as viewed in FIG. 6) and can act as a bearing surface for a head 64 of a femoral component 66 (FIG. 9) so as to dissipate stresses over the entire bearing 22. A second interlocking portion 70 can be formed around a rim portion 72 of the bearing 22. In the example shown, the second interlocking portion 70 is in the form of complementary lobbed notches 74 defined around the rim portion 72. The first and second interlocking portions 40 and 70 can cooperatively mate in an assembled position (FIG. 4) such that the lobbed fingers 42 nest with the lobbed notches 74 and, therefore, inhibit rotational motion of the bearing 22 within the acetabular cup 20. In the particular example shown, the lobbed notches 74 outnumber the lobbed fingers 42 by a factor of two. It is appreciated that other configurations may be used.

The ring 24 will now be described in greater detail. The ring 24 may be formed of any suitable biocompatible material. In one example, the ring 24 may be formed of similar material found in the locking ring offered in the RingLoc® system offered by Biomet, Inc., of Warsaw, Ind. The ring 24 can generally define a radial body 78 defining a discontinuation or slit 80. As will become appreciated, the material properties of the ring 24 should be selected such that the ring 24 is permitted to flex in a radial direction toward its outer perimeter upon an applied force and return to a static position upon removal of the force.

A pair of fingers 82 can be formed at opposing portions of the slit 80. The fingers 82 can extend outboard relative to a circumferential outer surface of the radial body 78. An annular protrusion 84 can be integrally formed on the ring 24. In one example, the annular protrusion 84 can be diametrically opposed to the fingers 82. As explained, the ring 24 can be adapted to locate within the inboard annular groove 46 of the acetabular cup 20. In the locked position, the inboard annular groove 46 of the acetabular cup 20 is operable to snappingly receive the ring 24 to secure the bearing 22 within the concave surface of the acetabular cup 20. Explained further, the ring 24 can be adapted to partially nest within the inboard annular groove 46 of the acetabular cup 20 and, concurrently, partially nest within the outboard annular groove 62 of the bearing 22 in the locked position. The annular protrusion 84 of the ring 24 can nest within the second slot 52. In this way, the ring 24 may be discouraged from rotating around a longitudinal axis of the acetabular cup 20.

Figure 2:
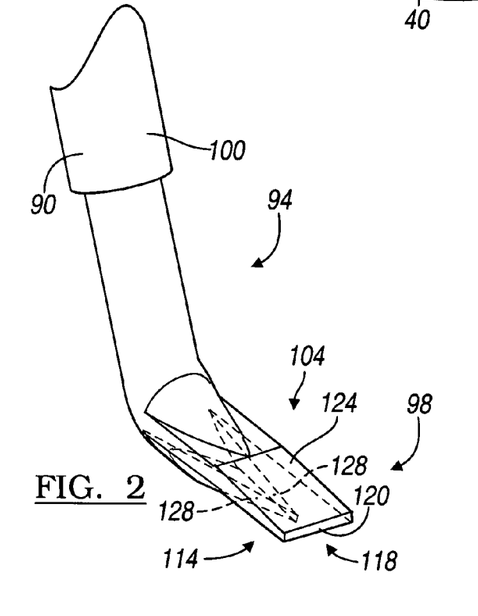
FIG. 2 is a top perspective view of a distal end of the removal tool of FIG. 1.
Figure 3:
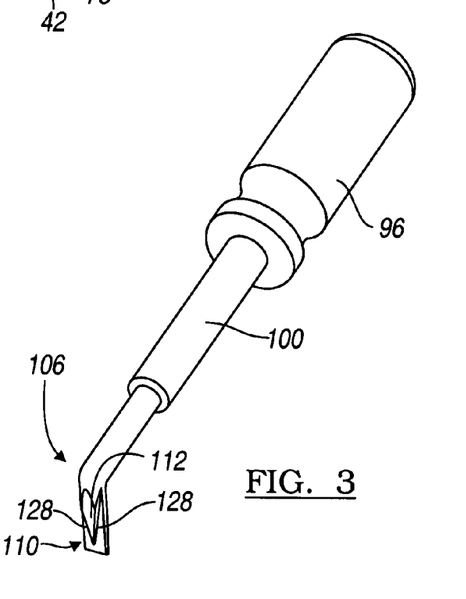
FIG. 3 is a bottom perspective view of the distal end of the removal tool of FIG. 1.

With reference now to FIGS. 1-3, the removal tool 14 will be described in greater detail. In general, the removal tool 14 can include a longitudinal body 90 having a proximal end 92 and a distal end 94. The proximal end 92 can include a handle 96 disposed thereon. The distal end 94 can include an engaging portion 98. In one example, the engaging portion 98 can be defined at an angle relative to a longitudinal axis of the longitudinal body 90. The longitudinal body 90 can define a shaft 100 extending between the handle 96 and the distal end 94.

The distal end 94 can further define an upper portion 104 (FIG. 2) and a lower portion 106 (FIG. 3). The lower portion 106 can define a ring engaging portion 110 having a ring engaging surface 112. A terminal end 114 of the removal tool 14 can define a bearing engaging portion 118 having a bearing engaging surface 120. The distal end 94 can include an intermediate section 122 defined between the longitudinal body 90 and a sloped section 124.

The ring engaging surface 112 can be further defined by a pair of outwardly ramped surfaces 128. The outwardly ramped surfaces 128 can slope generally outward from the lower portion 106 toward the upper portion 104.

An exemplary method of removing the ring 24 and bearing 22 with the removal tool 14 will now be described. With initial reference to FIG. 4, the acetabular cup assembly 12 is shown with the ring 24 nested within the inboard annular groove 46 of the acetabular cup 20 and the bearing 22 secured within the bearing engaging surface 38 of the acetabular cup 20 (locked position). As shown, one of the lobbed notches 74 of the bearing 22 can provide access to an upper surface of the ring 24 at the pair of fingers 82. Also, notably, the first slot 50 can be substantially aligned with and provides additional access to the fingers 82. Once the ring engaging portion 110 of the removal tool 14 has been located atop the ring 24 at the fingers 82, downward force (as viewed in FIG. 4) may be applied by the removal tool 14 at the slit 80 of the ring 24. The downward force of the removal tool 14 encourages the outwardly ramped surfaces 128 of the removal tool 14 to ride along the opposing surfaces of the slit 80 and, therefore, incrementally urge the ring 24 to spread radially outward toward an unlocked position. It is appreciated that sufficient outward clearance exists in the inboard annular groove 46 of the acetabular cup 20 to accommodate initial outward radial movement of the ring 24. Once the ring 24 has flexed radially outward a predetermined amount, the ring 24 can be substantially displaced from the outboard annular groove 62 of the bearing 22.

Figure 7:
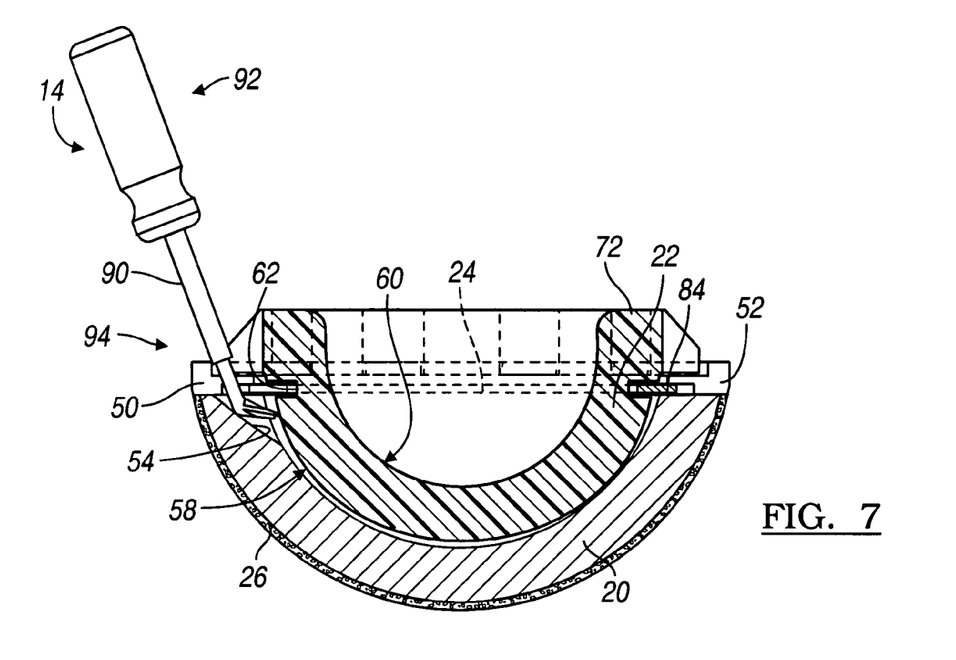
FIG. 7 is the sectional view of FIG. 6 shown with the distal end of the tool engaging the bearing.
Figure 8:
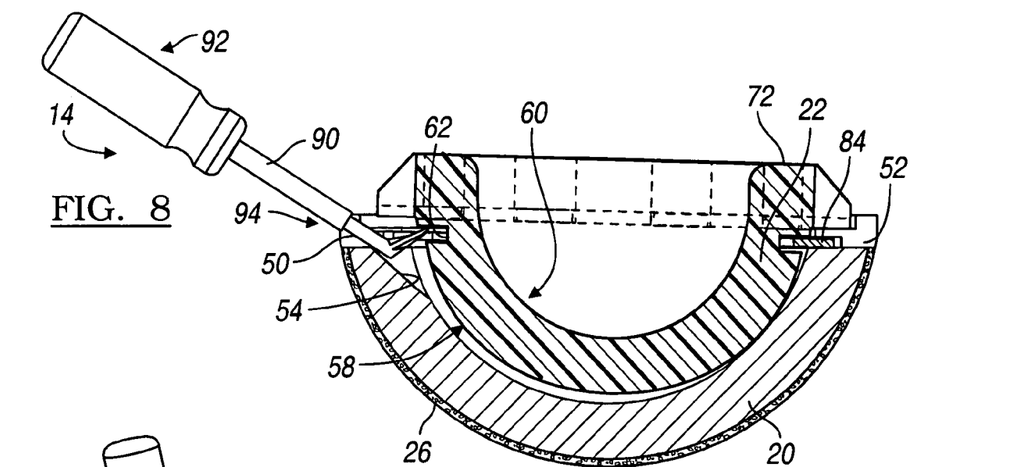
FIG. 8 is the sectional view of FIG. 7 shown with the distal end of the tool tilted and urging the bearing away from the cup.

With the ring 24 still in an outwardly flexed position, the removal tool 14 can then be tilted in a direction counterclockwise, as viewed in FIGS. 7 and 8. As a result, the bearing engaging surface 120 of the distal end 94 of the removal tool 14 can engage the bearing 22 and exert a prying action (i.e., in a direction toward the rim portion 72) to further encourage the bearing 22 to remove from the acetabular cup 20 (i.e., as illustrated in the sequence from FIG. 7 and FIG. 8). It is important to note that the interaction of the removal tool 14 with the bearing 22 (i.e., at the bearing engaging surface 120) does not substantially deface the bearing 22.

Figure 18:
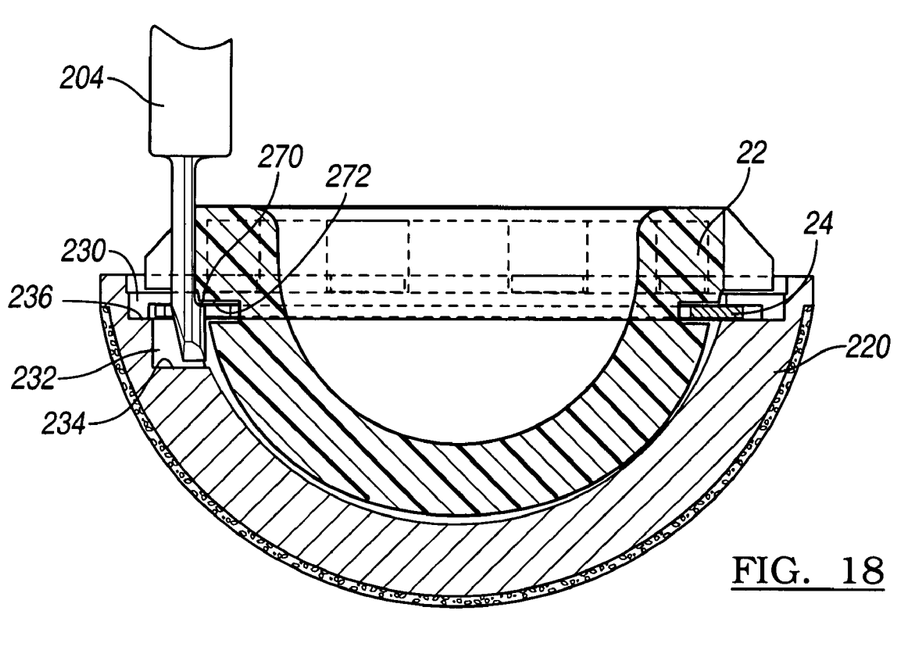
FIG. 18 is a sectional view of the acetabular cup assembly taken along line 18-18 of FIG. 17 shown with the removal tool inserted into the notch.

Turning now to FIGS. 10-18, a system 200 for replacing a portion of a hip joint according to additional features is shown. The system 200 can generally include an acetabular cup assembly 202 and a removal tool 204. The acetabular cup assembly 202 can include an acetabular cup 220 a bearing 22, and a ring 24. The acetabular cup 220 can be substantially similar to the acetabular cup 20 described above. The acetabular cup 220 can include a first slot 230 and a cavity 232. The slot 230 and the cavity 232 can be positioned inboard of a continuous rim portion. The cavity 232 can define a terminal surface 234 substantially perpendicular to an upper surface 236 of the slot (FIG. 18). As will be described, the removal tool 204 can be adapted to engage the ring 24 and operatively spread the ring 24 to an unlocked position, and subsequently lift the bearing away from the acetabular cup 220.

Figure 13:
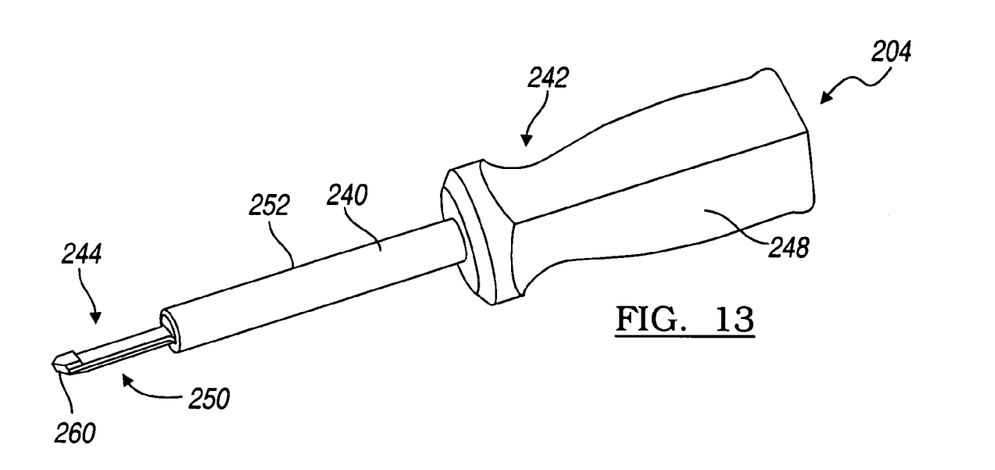
FIG. 13 is a perspective view of the removal tool.
Figure 14:
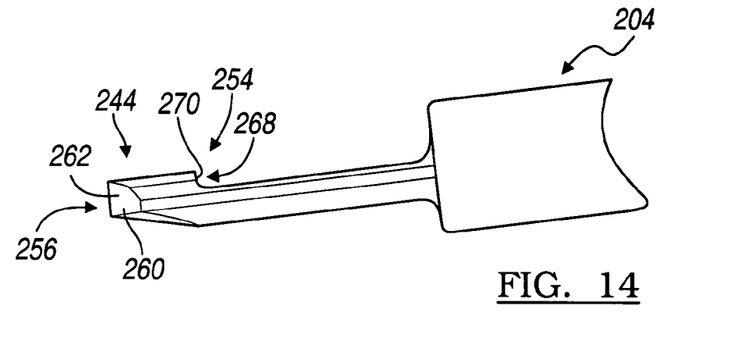
FIG. 14 is a side view of the distal end of the removal tool of FIG. 13.

With reference now to FIGS. 13 and 14, the removal tool 204 will be described in greater detail. In general, the removal tool 204 can include a longitudinal body 240 having a proximal end 242 and a distal end 244. The proximal end 242 can include a handle 248 disposed thereon. The distal end 244 can include an engaging portion 250. The longitudinal body 240 can define a shaft 252 extending between the handle 248 and the distal end 244.

Figure 15:
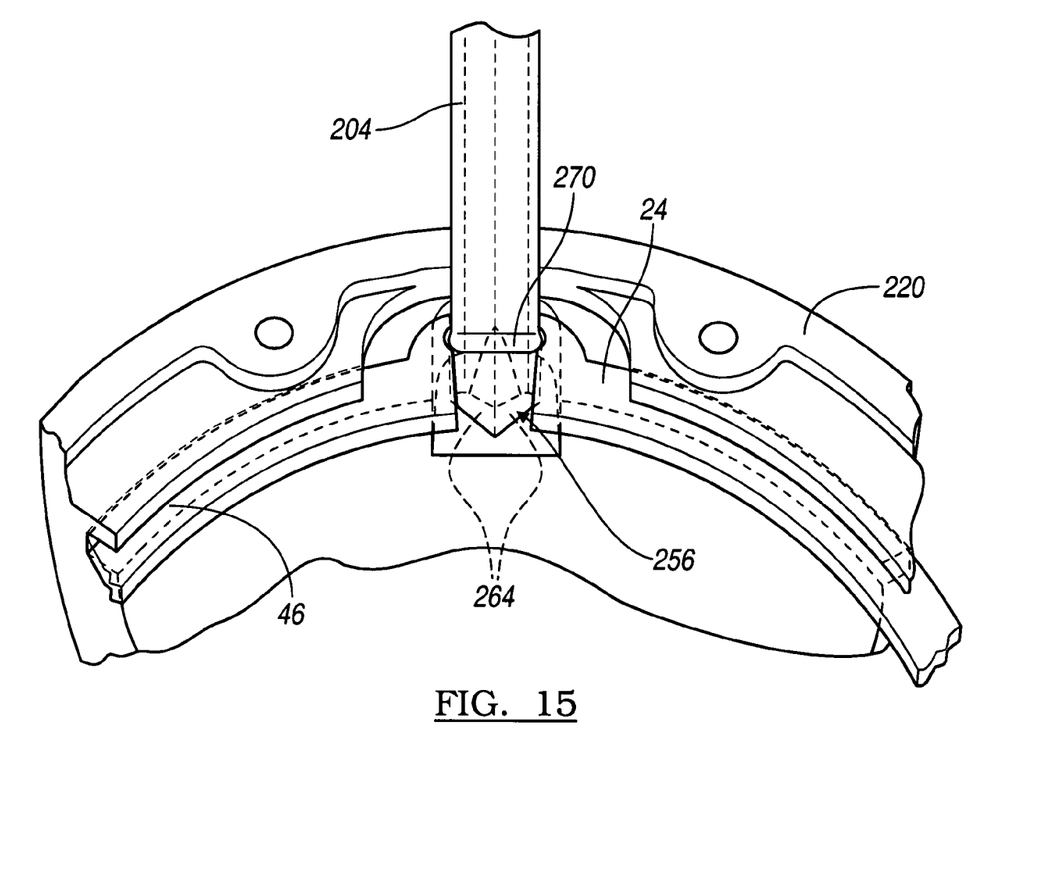
FIG. 15 is a partial perspective view of the acetabular cup assembly shown with the bearing in a locked position within the acetabular cup and the distal end of the removal tool initially engaged with a slit defined in the ring.

The distal end 244 can further define an upper portion 254 and a lower portion 256. The lower portion 256 can define a ring engaging portion 260 having a ring engaging surface 262. The ring engaging surface 262 can be further defined by a pair of outwardly ramped surfaces 264 (FIG. 15). The outwardly ramped surfaces 264 can slope generally outward from the lower portion 256 toward the upper portion 254. The upper portion 254 can include a bearing engaging portion 268 having an engagement lip 270 adapted to engage an underside surface 272 (FIG. 18) of the bearing 24.

Figure 12:
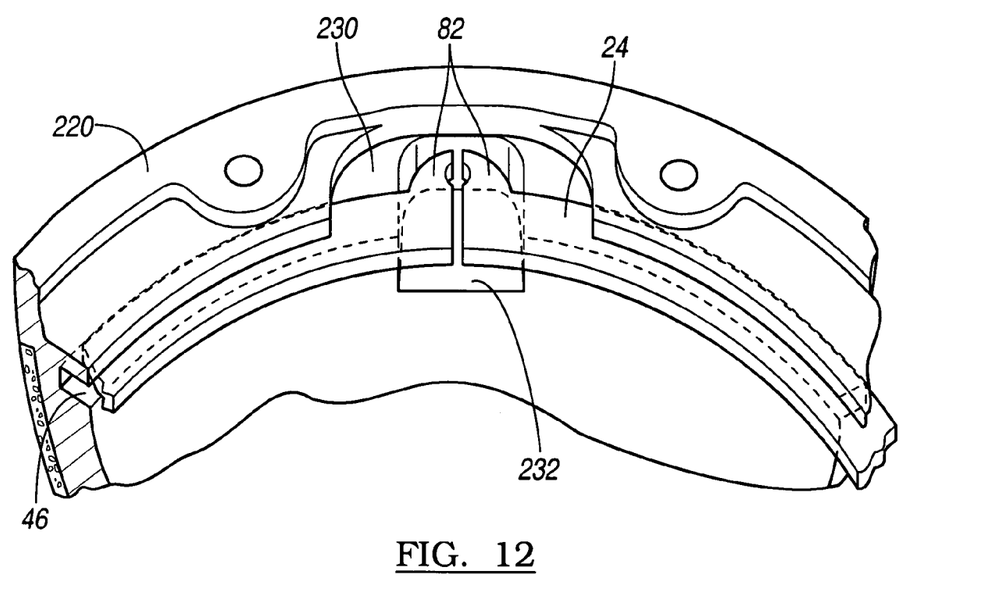
FIG. 12 is a partial perspective view of the acetabular cup of FIG. 11 shown with the ring in an installed position.

An exemplary method of removing the ring 24 and the bearing 22 with the removal tool 204 will now be described. With reference to FIG. 12, the acetabular cup assembly 202 is shown with the ring 24 nested within the inboard annular groove 46 of the acetabular cup. The bearing 22 is not shown in FIG. 12 for illustrative purposes but is shown installed in the locked position in FIGS. 17 and 18. As shown, the first slot 230 can be substantially aligned with and provides additional access to the fingers 82.

Once the ring engaging portion 260 of the removal tool 204 has been located atop the ring 24 at the fingers 82, downward force (as viewed in FIG. 10) may be applied by the removal tool 204 at the slit 80 of the ring 24. It is important to note that at this time, the bearing 22 is still in a nested position with the cup 220 (as shown in FIG. 18). The bearing 22 is shown slightly elevated in FIG. 10 simply to shown the interaction between the tool 204 and the ring 24. The downward force of the removal tool 204 encourages the outwardly ramped surfaces 264 of the removal tool 204 to ride along the opposing surfaces of the slit 80 and, therefore, incrementally urge the ring 24 to spread radially outward toward an unlocked position. It is appreciated that sufficient outward clearance exists in the inboard annular groove 46 of the acetabular cup 220 to accommodate initial outward radial movement of the ring 24. Once the ring 24 has flexed radially outward a predetermined amount, the ring 24 can be substantially displaced from the outboard annular groove 62 of the bearing 22.

Figure 16:
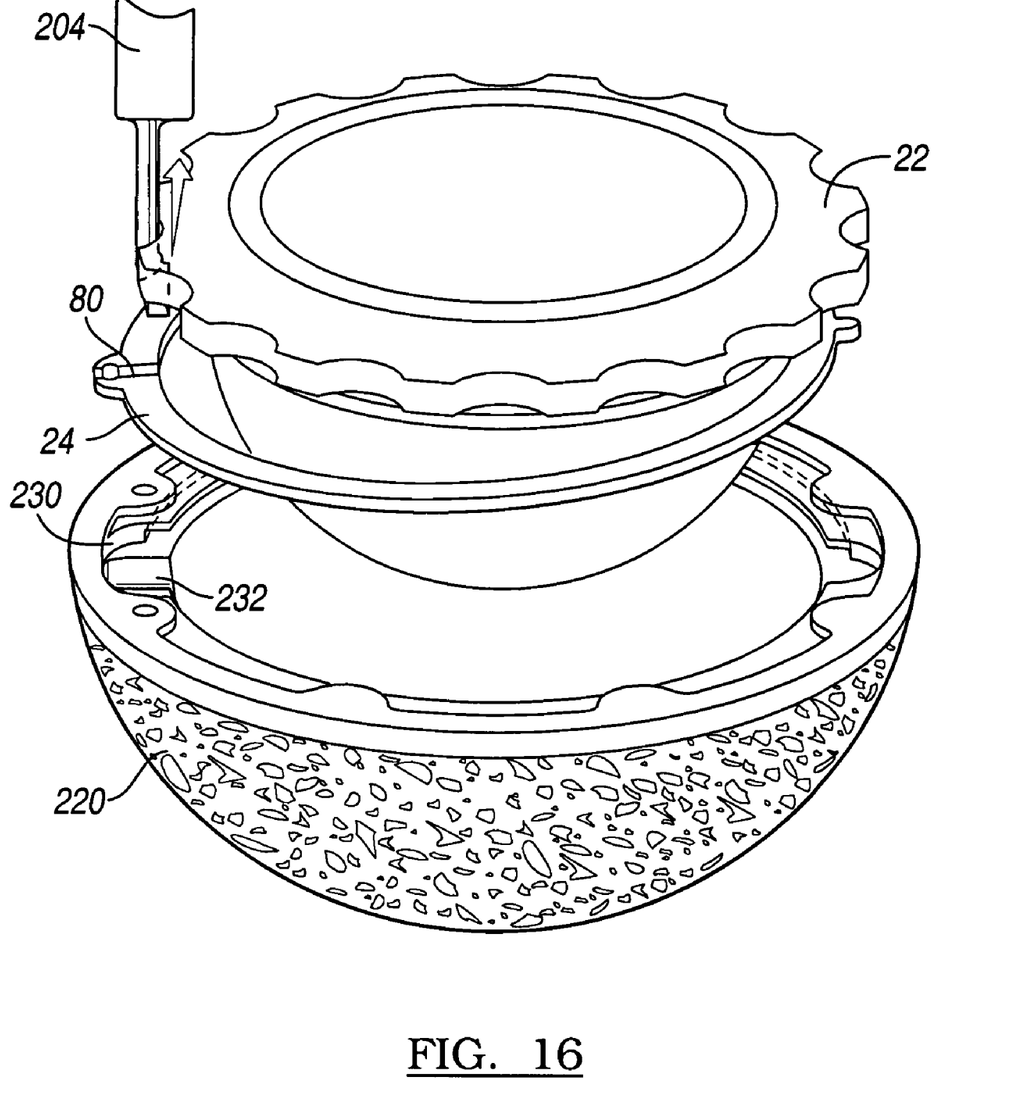
FIG. 16 is a perspective view of the acetabular cup assembly and removal tool subsequent to removal of the ring and the bearing.
Figure 17:
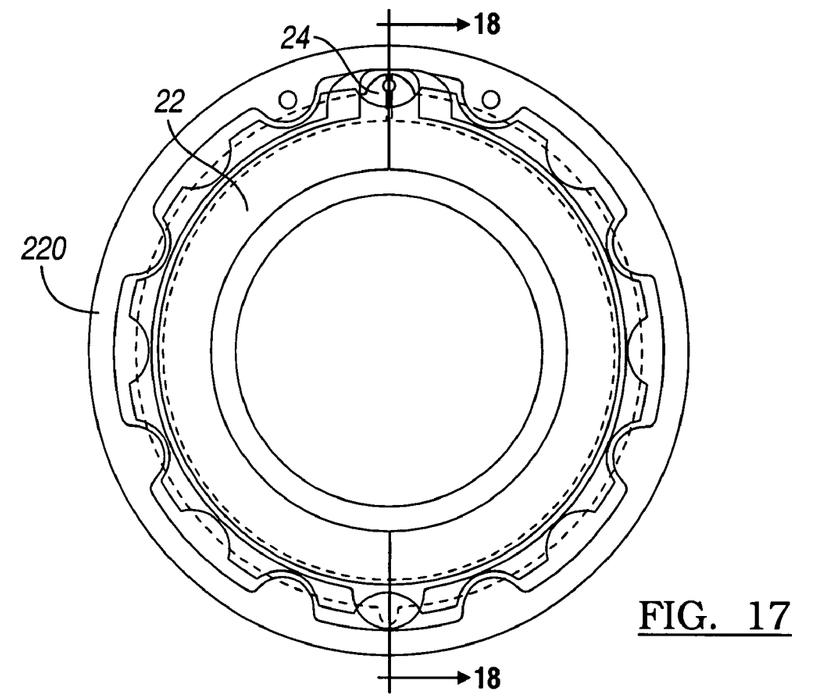
FIG. 17 is a plan view of the acetabular cup assembly.

With the ring 24 still in an outwardly flexed position, the removal tool 204 can then be translated upwardly (as viewed in FIG. 18) along a longitudinal axis of the tool 204. During the upward translation, the engagement lip 270 engages the underside surface 272 of the bearing 22 to lift the bearing 22 away from the cup 220 (FIG. 16). It is appreciated that translation about the longitudinal axis of the tool 204 may be advantageous in such minimally invasive surroundings. In another example, the tool 204 may additionally or alternatively rotate about its longitudinal axis to provide a prying action to the bearing 22.

While the disclosure has been described in the specification and illustrated in the drawings with reference to various embodiments, it will be understood by those skilled in the art that various changes may be made and equivalents may be substituted for elements thereof without departing from the scope of the invention as defined in the claims. Furthermore, the mixing and matching of features, elements and/or functions between various embodiments is expressly contemplated herein so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the disclosure without departing from the essential scope thereof. Therefore, it is intended that the invention not be limited to the particular embodiment illustrated by the drawings and described in the specification as the best mode presently contemplated for carrying out this disclosure, but that the disclosure will include any embodiments falling within the foregoing description and the appended claims.

What is claimed is:

1. A system for replacing a portion of a hip joint comprising:

a cup having an outer acetabulum engaging surface, an inner bearing facing surface and an upper rim portion, said upper rim portion including a slot having a ramped surface that slopes downward to said inner bearing facing surface, said outer surface engagable to an acetabulum;

a bearing having an outer bearing surface and an inner articulating surface, said outer bearing surface positioned adjacent said inner bearing facing surface;

a ring selectively disposed between said cup and said bearing, said ring including an annular body having a slit formed therein, said ring movable between a locked position and an unlocked position wherein said ring retains said bearing relative to said cup in said locked position; and a removal tool having a proximal end and a distal end, said distal end defining having a ring engaging surface and a bearing engaging surface, said ring engaging surface adapted to engage said ring at said slit such that said ring expands radially from said locked position away from engagement with said bearing to said unlocked position, said bearing engaging surface configured to engage said ramped surface, adapted to engage said bearing and urge said bearing away from said cup.

2. The system of claim 1, wherein said ring includes a pair of fingers formed at opposing portions of said slit, said fingers adapted to locate at said first slot in said cup in said locked position wherein said fingers are positioned in said slot generally above and spaced apart from said ramped surface in said locked position.

3. The system of claim 2 wherein said upper rim of said cup further defines a second slot formed therein and adapted to locate an annular protrusion formed on said ring in said locked position.

4. The system of claim 2 wherein said ring engaging surface of said removal tool includes a pair of converging sloped surfaces adapted to slidably engage said pair of fingers and thereby spread said ring radially toward said unlocked position.

5. The system of claim 2 wherein said distal end of said tool is accommodated by said ramped surface of said slot such that said distal end of said tool locates at a position between said fingers and said ramped surface as said bearing engaging surface engages said bearing.

6. The system of claim 2 wherein an upper portion of said bearing and said rim of said cup provide complementary interlocking portions adapted to inhibit rotation of said bearing within said cup in said locked position.

7. The system of claim 1 wherein said distal end of said removal tool defines an angle relative to said proximal end of said tool wherein rotation of said removal tool at said proximal end imparts a prying action at said bearing engaging surface of said distal end onto said bearing.

8. The system of claim 1 wherein said distal end of said removal tool defines an engagement lip at said bearing engaging surface.

9. The system of claim 8 wherein said engagement lip is adapted to engage an underside surface of said bearing upon expansion of said ring to said unlocked position.

10. The system of claim 9 wherein said engagement lip imparts a force on said underside of said bearing upon movement of said removal tool away from said cup in a direction along a longitudinal axis of said removal tool.

11. A system for replacing a portion of a hip joint comprising:
a cup having a first surface engagable to an acetabulum and including an upper rim portion having a first slot formed thereon, said slot formed from an outer face of said cup to an inboard portion of said cup, said cup further including a ramped surface located in said slot that slopes downward to an inner bearing engaging surface of said cup;
a bearing having an outer surface positioned adjacent said cup;
a ring selectively disposed between said cup and said bearing and movable between a locked position and an unlocked position, wherein said ring retains said bearing relative to said cup in said locked position, wherein in said locked position said ramped surface slopes beneath a portion of said ring aligned with said slot; and
a removal tool having a proximal end and a distal end and defining a substantially longitudinal body, said distal end having a ring engaging surface including a pair of sloped surfaces that slidably engage said ring at said slit such that said ring expands radially from said locked position to said unlocked position and a bearing engaging surface configured to engage said ramped surface.

12. The system of claim 11 wherein said distal end of said removal tool includes a bearing engaging surface including an engagement lip and wherein said pair of sloped surfaces at said distal end of said tool converge.

13. The system of claim 11 wherein said engagement lip is adapted to engage an underside surface of said bearing upon expansion of said ring to said unlocked position.

14. The system of claim 13 wherein said engagement lip imparts a force on said underside of said bearing upon movement of said removal tool away from said cup in a direction along a longitudinal axis of said removal tool.

15. The system of claim 14 wherein said distal end and said proximal end are substantially collinear.

16. The system of claim 11 wherein said ring includes a pair of fingers formed at opposing portions of said slit, said fingers adapted to locate at said first slot in said cup in said locked position.

17. The system of claim 16 wherein said first slot is formed in an upper rim of said cup that further defines a second slot formed therein and adapted to locate an annular protrusion formed on said ring in said locked position.

18. A system for replacing a portion of a hip joint comprising:
a cup having a first surface engagable to an acetabulum and including a continuous upper rim portion having a first slot including an upper surface, said continuous upper rim portion defining a cavity formed below said first slot and a second slot formed inboard of said continuous outer rim;
a bearing having an outer surface positioned adjacent said cup and an inner articulating surface;
a ring selectively disposed between said cup and said bearing and movable between a locked position and an unlocked position wherein said ring retains said bearing relative to said cup in said locked position, said ring including an annular body defining a slit formed between a pair of arms and including a protrusion adapted to locate in said second slot and inhibit rotation of said ring in said locked position, said pair of arms configured to rest on said upper surface of said first slot in said locked position; and
a removal tool having a proximal end and a distal end, said distal end having a ring engaging surface and a bearing engaging surface, said ring engaging surface including converging ramped surfaces that engage said ring at said slit such that said ring expands radially from said locked position away from engagement with said bearing to said unlocked position while said ring engaging surface passes into said cavity, said bearing engaging surface adapted to engage said bearing and urge said bearing away from said cup.

19. The system of claim 18 wherein said bearing engaging surface includes an engagement lip that is adapted to engage an underside surface of said bearing upon expansion of said ring to said unlocked position.

20. The system of claim 19 wherein said engagement lip imparts a force on said underside of said bearing upon movement of said removal tool away from said cup in a direction along a longitudinal axis of said removal tool.

21. The system of claim 20 wherein said distal end and said proximal end are substantially collinear.

* * * * *

UNITED STATES PATENT AND TRADEMARK OFFICE
CERTIFICATE OF CORRECTION

PATENT NO.         : 7,572,294 B2
APPLICATION NO. : 11/714991
DATED               : August 11, 2009
INVENTOR(S)       : Meridew et al.

It is certified that error appears in the above-identified patent and that said Letters Patent is hereby corrected as shown below:

Column 3, line 31, USSN 11/111,123 should be "11/709,549".

Column 5, line 62, delete "defining" before "having" as shown in the Amendment dated January 15, 2009 (page 2, line 15, claim 1).

Column 5, line 67, delete "shown" and replace with "show".

Signed and Sealed this

Seventeenth Day of November, 2009

David J. Kappos
*Director of the United States Patent and Trademark Office*